United States Patent [19]

Coates

[11] 4,213,000

[45] Jul. 15, 1980

[54] REDUCING COLOR FORMERS IN 1,4-BUTANEDIOL

[75] Inventor: John S. Coates, Newark, Del.

[73] Assignee: E. I. Du Pont de Nemours and Company, Wilmington, Del.

[21] Appl. No.: 42,945

[22] Filed: May 29, 1979

[51] Int. Cl.$^2$ .................... C07C 31/20; C07C 29/24
[52] U.S. Cl. .................................. 568/861; 568/868
[58] Field of Search ............................. 568/861, 868

[56] References Cited

U.S. PATENT DOCUMENTS

| | | | |
|---|---|---|---|
| 2,768,214 | 10/1956 | McKinley et al. | 568/868 |
| 2,950,326 | 8/1960 | Hort | 568/861 |
| 2,953,605 | 9/1960 | Hort | 568/861 |
| 2,967,893 | 1/1961 | Hort et al. | 568/861 |
| 3,449,445 | 6/1969 | Wetherill | 568/861 |
| 3,950,441 | 4/1976 | Rudoff et al. | 568/861 |
| 4,048,116 | 9/1977 | Voges et al. | 568/861 |

*Primary Examiner*—Joseph E. Evans

[57] ABSTRACT

1,4-Butynediol is catalytically hydrogenated under conventional conditions to produce a reaction product containing 1,4-butanediol. This reaction product is then hydrogenated under acid conditions, i.e., pH 1-6 and temperatures of 120°-150° C., to produce a 1,4-butanediol product. Upon further separation, the 1,4-butanediol is practically free from compounds that would produce color when the diol is used to make polyesters.

7 Claims, No Drawings

REDUCING COLOR FORMERS IN 1,4-BUTANEDIOL

DESCRIPTION

1. Technical Field

This invention relates to a process for reducing the color-forming bodies in 1,4-butanediol. More specifically, this invention relates to a process for reducing the color-forming bodies in 1,4-butanediol by subjecting the reaction product from the catalytic hydrogenation of 1,4-butynediol to further treatment under hydrogenation conditions at a pH of 1-6.

2. Background Art

Processes for the catalytic hydrogenation of 1,4-butynediol (2-butyne-1,4-diol) to 1,4-butanediol are known in the art, for example, U.S. Pat. Nos. 2,967,893; 3,691,093 and 3,617,567 disclose the hydrogenation of aqueous 1,4-butynediol to 1,4-butanediol. This catalytic hydrogenation can be conducted in one or two steps and U.S. Pat. Nos. 2,967,893; 3,449,445; 3,950,441 and 4,048,116 disclose two-step hydrogenation processes.

The 1,4-butanediol that generally results from the hydrogenation of 1,4-butynediol does not appear to possess any color bodies when visually examined after purification. However, often color-forming bodies or their precursors are present and they become visible when the diol is used to make polyesters.

Purification or removal of undesirable compounds from 1,4-butanediol by various processes including distillation are known in the art. These processes are either very costly and/or do not result in reducing sufficient color-forming bodies to avoid undesirable color formation when the 1,4-butanediol is used to prepare a polyester.

DISCLOSURE OF THE INVENTION

A process has been discovered for reducing the color-forming compounds in 1,4-butanediol. This process involves a two-stage hydrogenation, i.e., a first stage conventional hydrogenation and a second hydrogenation under acid conditions.

In the first stage 1,4-butynediol is catalytically hydrogenated to form a reaction product containing 1,4-butanediol under conventional conditions. The hydrogenation reaction product is then treated under hydrogenation conditions at a pH of 1-6, preferably 4-6, most preferably 4-5, and a temperature of 115°-200° C., preferably 120°-150° C. and most preferably 130°-150° C. This second stage hydrogenation under acid conditions results in a 1,4-butanediol that after conventional purification has reduced color formers. The diol can then be used to make color-free polyesters.

The catalytic hydrogenation of 1,4-butynediol is known in the art and can be carried out with an aqueous solution of 1,4-butynediol or a solution of the butynediol in an inert solvent. Some form of agitation is usually employed in the reaction vessel to provide the desired contact between the reaction medium and the hydrogen. The pH of the butynediol solution may vary; and generally, it ranges from 7-12 as hydrogenation under acidic conditions may result in the formation of undesired byproducts. After hydrogenation, the pH of the reaction product is generally alkaline or about 7-9.

The catalyst used in either the first or second stage hydrogenation may be any metal or metal compounds of the type well known and customarily referred to in the art as hydrogenation catalysts. It is desirable to employ as the hydrogenation catalyst a metal or a compound of a metal that may be easily and economically prepared, which has a high degree of activity and which retains its activity under the conditions of the process for a length of time sufficient to avoid the necessity of reactivating or replacing the catalyst at frequent intervals. Generally speaking, hydrogenation catalysts which may be employed in the execution of the process of the invention include the metal hydrogenation catalysts, such as platinum, palladium, gold, silver, copper, vanadium, tungsten, cobalt, nickel, ruthenium, rhodium, manganese, chromium, molybdenum, iridium, titanium, zirconium and the like and mixtures of the same and compounds and alloys thereof, particularly oxides and sulfides. Because of the ease and economy with which they may be prepared, the base metal hydrogenation catalysts, particularly the pyrophoric base metal hydrogenation catalysts such as nickel, cobalt and iron, are advantageous. Most important are nickel-aluminum alloys which are activated by partial removal of the aluminum with alkali. A nickel-containing foraminous material particularly adaptable is described, e.g., in U.S. Pat. Nos. 3,627,790 and 2,950,260.

Activation of a nickel-aluminum alloy catalyst is generally carried out by treating the alloy with a dilute aqueous alkali solution which is fed at a temperature not in excess of 35° C. whereby not more than about 1.5 moles of hydrogen are evolved for each mole of alkali. Alkali metal hydroxides such as sodium, potassium and lithium hydroxide are suitable for this use. Preferably, the alkali is an aqueous solution containing about 0.25–1% by weight of sodium hydroxide and the exit temperature of the solution during activation does not exceed about 35° C. It is preferable to remove about 10–30% of the aluminum originally contained in the alloy since the resulting catalyst retains its efficiency somewhat longer than alloys activated by the removal of less aluminum.

The hydrogenation catalyst may be employed in a finely divided form and dispersed in and throughout the reaction mixture, or it may be employed in a more massive state, e.g., fixed bed, either in essentially the pure state or supported upon or carried by an inert or catalytically active supporting or carrier material, such as pumice, kieselguhr, diatomaceous earth, clay, alumina, charcoal, carbon or the like and the reaction mixture contacted therewith as by flowing the mixture over or through a bed of the catalyst or according to other methods that are known in the art.

The hydrogenation reaction in the first stage is generally carried out at a hydrogen partial pressure of about 2500–5500 psi and a superficial gas velocity of at least about 0.5 foot per minute measured at the hydrogen exit from the catalyst bed. With hydrogen pressures of less than about 2500 psi, uneconomically large amounts of catalyst are required, the amount of intermediate 2-butene-1,4-diol, hereinafter referred to as butenediol, contained in the product increases significantly, and the catalyst is quickly deactivated. Pressures above about 5000 psi are not economical because they require special high pressure equipment. Preferably the hydrogen partial pressure is about 3000–5000 psi and the superficial gas velocity is at least about 0.8 foot per minute. The first stage hydrogenation is continued until the desired level of butenediol is obtained in the reaction product; this amount will vary depending on the requirements of the subsequent steps in the process. In most embodiments it will be desirable to reduce the amount of butenediol in the product to substantially zero.

The hydrogenation temperature in the first stage may vary from about 60°–150° C. When the temperature is less than about 60° C., uneconomically large amounts of catalyst are required to initiate the reaction. Since the reaction is exothermic, the temperature measured at the hydrogenation reactor exit will be somewhat higher than at the reactor entrance. The temperature at the reactor exit should not exceed about 150° C. At temperatures above about 150° C., byproduct formation, principally n-butanol, becomes excessive. Preferably, the reaction temperature is maintained at about 70°–145° C.

Since the first stage hydrogenation reaction is exothermic, it is necessary that heat be removed from the reaction. This is conveniently accomplished by recycling a major portion of the reactor effluent back to the reactor with heat removal from the recycle stream. Preferably, the recycle to fresh feed ratio is about 10–40:1, that is, in the range of about 10:1 to about 40:1. Most preferably, the recycle to fresh feed ratio is about 15°–25:1. Within this recycle range the temperature of the reactants fed to the reactor is preferably maintained at about 70°–125° C. With a recycle to fresh feed ratio of about 20:1, the temperature of the reactants fed to the reactor can be maintained constant by reducing the temperature of the recycle stream by about 23° C.

Of course, the invention is not limited to a recycle process since other methods of removing heat can be used. For example, the reaction could be carried out stepwise with heat removal between the steps. Inert diluents or excess hydrogen could also be used to further reduce the amount of exotherm.

When using the preferred activated nickel-aluminum catalysts in the first stage, the reaction should be conducted under nonacidic conditions to avoid the generation of undesired byproducts. Accordingly, it is preferred that alkali be added to the reactants in sufficient amount to maintain a pH of about 7–12 at the reactor exit. The pH is specified "at the reactor exit" because it has been observed that the pH sometimes varies between the reactor entrance and the reactor exit. Control of the pH may be accomplished by adding alkali to the fresh butynediol feed, by adding alkali to the reactor effluent being recycled, or both. Suitable alkali for this use includes alkali metal hydroxides such as sodium, potassium and lithium hydroxides, alkali metal carbonates and the like.

As previously set forth, the first stage hydrogenation should be carried out so as to convert butynediol to saturated products as completely as possible within practical limits. The presence of butenediol in the hydrogenation product results in the formation of 2,5-dihydrofuran, hereinafter referred to as dihydrofuran, an undesirable impurity. It is particularly desirable, therefore, that the amount of butenediol in the product be reduced to substantially zero in the hydrogenation process of this invention.

The first stage hydrogenation can be carried out in one step or, if desired, in two or more steps. In a two-step embodiment, butynediol is passed to a primary hydrogenation step employing recycle; and the product of this step, containing some butenediol, is passed to a supplemental hydrogenation step using the same type of catalyst and conditions, but without recycle, to form a final product which is substantially free of butenediol. In this case it is preferred that the butenediol content of the product of the first step be reduced to a very low level. The butenediol content of the first step product should be maintained low enough that the temperature in the second step can be controlled during conversion of the remaining butenediol to butanediol without recycle being necessary.

In the process of the invention the reaction product from the conventional hydrogenation reaction of the first stage is further treated under the same hydrogenation conditions except that the pH is 1–6, preferably 4–6 and most preferably 4–5, and the temperature is 115°–200° C., preferably 120°–150° C. This higher temperature is employed to hydrolyze any acetals present. The second stage hydrogenation is continued until the desired reduction in color formers is obtained.

The pH of 1–6 is attained by the addition of acid to the reaction product. A wide range of acids may be used. Some examples of such acids include mineral acids such as sulfuric, phosphoric, nitric and the like acids or such acid-acting salts as aluminum sulfate and the like or water-soluble organic carboxylic acids such as acetic, propionic, isobutyric and n-butyric acids and polycarboxylic acids such as succinic, malonic and adipic acids and the like. At pH values about 6, the color-forming bodies are not sufficiently reduced. At pH values from 1–4, some attacking of some of the hydrogenation catalyst can occur. However, with some hydrogenation catalyst, e.g., a noble metal catalyst, this is not a serious problem.

The reaction product from the second stage acid hydrogenation comprises 1,4-butanediol, water and other impurities. The 1,4-butanediol, after being separated from the reaction product in the conventional manner, has a high purity and when reacted with a suitable acid, e.g., adipic acid, forms a polyester that is essentially free of color. Generally, the separation of 1,4-butanediol from the reaction product is by distillation.

EXAMPLES

The examples that follow further illustrate the process of the invention. All percentages in the examples are by weight unless otherwise indicated.

EXAMPLES 1–3

A solution of 1,4-butanediol in water was prepared by hydrogenating a 40% solution of crude 1,4-butynediol in water (prepared from the reaction of acetylene and formaldehyde) over a Raney nickel catalyst at 100° C. with 4500 psig $H_2$ at pH 8. This material was then subjected to second stage hydrogenation over Raney nickel at 130° C. with 3000 psig $H_2$. This was carried out first, as a control run with no adjustment of pH, and then at a series of three pH levels as indicated below with the pH adjusted by addition of sulfuric acid to the different samples The crude butanediol solutions were distilled, and the refined butanediol samples were converted to a polybutylene adipate polyester by reacting 90 g of the butanediol with 104 g of adipic acid at 180° C. in the absence of air for 7 hours. The APHA color values for the resulting polyesters were

|  | pH | Polyester APHA Color* |
|---|---|---|
| Control | 7 (no acid) | 120 |
| Ex 1 | 6 | 85 |
| Ex 2 | 5 | 40 |

| | pH | Polyester APHA Color* |
|---|---|---|
| Ex 3 | 4 | 20 |

*as determined by ASTM method D 1209.

I claim:

1. In the process for preparing 1,4-butane-diol by the catalytic hydrogenation of 1,4-butynediol the improvement comprising subjecting the hydrogenation reaction product to acid hydrogenation at a pH of 1-6 and a temperature of 115°-200° C.

2. The process of claim 1 wherein the pH is 4-5.

3. The process of claim 1 wherein the temperature is 120°-150° C.

4. In the process for preparing 1,4-butanediol by the catalytic hydrogenation of 1,4-butynediol at a temperature of 60°-150° C. and hydrogen pressure of 2500-5500 psig in the presence of a hydrogenation catalyst at a pH of 7-12 to form a hydrogenation reaction product containing 1,4-butanediol, the improvement comprising conducting an acid hydrogenation of the hydrogenation reaction product at a temperature of 115°-200° C., hydrogen pressure of 2500-5500 psig and a pH of 1-6 in the presence of a hydrogenation catalyst to form a reaction product containing 1,4-butanediol.

5. The process of claim 4 with the additional step of recovering the 1,4-butanediol by distillation.

6. The process of claim 4 wherein the acid hydrogenation is at a pH of 4-5.

7. The process of claim 4 wherein the temperature of the acid hydrogenation is 120°-150° C.

* * * * *